United States Patent [19]

Kolff

[11] 4,427,470
[45] Jan. 24, 1984

[54] VACUUM MOLDING TECHNIQUE FOR MANUFACTURING A VENTRICULAR ASSIST DEVICE

[75] Inventor: Willem J. Kolff, Salt Lake City, Utah
[73] Assignee: University of Utah, Salt Lake City, Utah
[21] Appl. No.: 298,420
[22] Filed: Sep. 1, 1981
[51] Int. Cl.$^3$ .............................................. A61F 1/24
[52] U.S. Cl. ...................................... 156/73.1; 3/1.7; 156/155; 156/245; 156/280; 156/285; 156/292; 156/289; 156/308.4; 264/545; 417/384; 427/233
[58] Field of Search ........................... 3/1.7; 417/384; 264/512, 545, 220; 427/236, 233; 156/155, 73.1, 156/212, 213, 245, 285, 292, 280, 308.4, 289

[56] References Cited

U.S. PATENT DOCUMENTS

| | | | |
|---|---|---|---|
| 2,315,394 | 3/1943 | Brosius | 156/155 |
| 2,873,227 | 2/1959 | Olson et al. | 156/213 |
| 2,917,751 | 12/1959 | Fry et al. | 3/1 |
| 3,097,366 | 7/1963 | Winchell | 3/1 |
| 3,152,340 | 10/1964 | Fry et al. | 3/1 |
| 3,182,335 | 5/1965 | Bolie | 3/1 |
| 3,206,768 | 9/1965 | Preston | 3/1 |
| 3,208,448 | 9/1965 | Woodward | 128/1 |
| 3,304,353 | 2/1967 | Harautuneian | 156/155 |
| 3,327,322 | 6/1967 | Norton | 3/1 |
| 3,379,191 | 4/1968 | Harvey | 128/1 |
| 3,478,695 | 11/1969 | Goranson et al. | 103/152 |
| 3,487,784 | 1/1970 | Rafferty et al. | 103/103 |
| 3,513,486 | 5/1970 | De Bennetot et al. | 3/1 |
| 3,518,702 | 7/1970 | La Russa | 3/1 |
| 3,534,409 | 10/1970 | Lance et al. | 3/1 |
| 3,541,612 | 11/1970 | Carney | 3/1 |
| 3,579,644 | 5/1971 | Esmond | 3/1 |
| 3,585,648 | 6/1971 | Suroff | 3/1 |
| 3,606,592 | 9/1971 | Madurski et al. | 417/413 |
| 3,636,570 | 1/1972 | Nielson | 3/1 |
| 3,647,324 | 3/1972 | Rafferty et al. | 417/420 |
| 3,663,966 | 5/1972 | Lavigne | 3/1 |
| 3,668,708 | 6/1972 | Thidal | 3/1 |
| 3,689,204 | 9/1972 | Prisk | 3/1.7 |
| 3,720,485 | 3/1973 | Holman, Jr. | 417/413 |
| 3,733,616 | 5/1973 | Willis, Jr. | 3/1 |
| 3,804,663 | 4/1974 | Clark | 427/233 |
| 3,969,175 | 7/1976 | Posner | 264/220 |
| 4,044,085 | 8/1977 | Graway | 156/155 |
| 4,222,127 | 9/1980 | Donachy et al. | 417/384 |
| 4,245,622 | 1/1981 | Hutchins | 3/1.7 |

FOREIGN PATENT DOCUMENTS

| | | |
|---|---|---|
| 14130 | 8/1980 | European Pat. Off. . |
| 2509006 | 9/1976 | Fed. Rep. of Germany . |
| 2716680 | 7/1978 | Fed. Rep. of Germany . |
| 7827088 | 4/1979 | France . |
| 660687 | 5/1979 | U.S.S.R. . |

OTHER PUBLICATIONS

Owen, D. R.; Galbraith, L. J.; and Kolff, W. J.: "New Prosthetic Device Fabrication Technique and its Use in Cardiac Prosthesis Development." Symposium 10th Annual Meeting International Biomaterials, 1978.

Zartnack, F.; Affeld, K.; and Bucherl, E. S.: "The Vacuum Molding Technique, A New Method For Fabricating Polyurethane Blood Pumps," Proceedings of the European Society of Artificial Organs, vol. VI; 99–103, 1979.

Primary Examiner—Jerome W. Massie
Attorney, Agent, or Firm—H. Ross Workman; Rick D. Nydegger; Dale E. Hulse

[57] ABSTRACT

A ventricular assist device and a method of manufacturing the ventricular assist device. The device is generally flat in shape and gently curved so that it may be comfortably implanted under the skin or inside the chest of a patient. The device includes a housing comprising an atrial blood chamber, an atrial compliance chamber, a ventricular blood chamber and a ventricular pumping chamber. Blood is introduced through an inlet port into the atrial blood chamber. An atrial compliance membrane within the housing separates the atrial blood chamber from the atrial compliance chamber and responds to the changing volume of blood. The ventricular blood chamber receives the blood from the atrial blood chamber through a flap valve which is formed as an integral extension of the compliance membrane. A pumping membrane within the housing separates the ventricular blood chamber from the ventricular pumping chamber and is displaced by a drive fluid to expel blood out of the ventricular blood chamber through an oulet port that is controlled by a second valve mechanism. The device is manufactured using a novel vacuum forming technique that is both simple and inexpensive.

26 Claims, 16 Drawing Figures

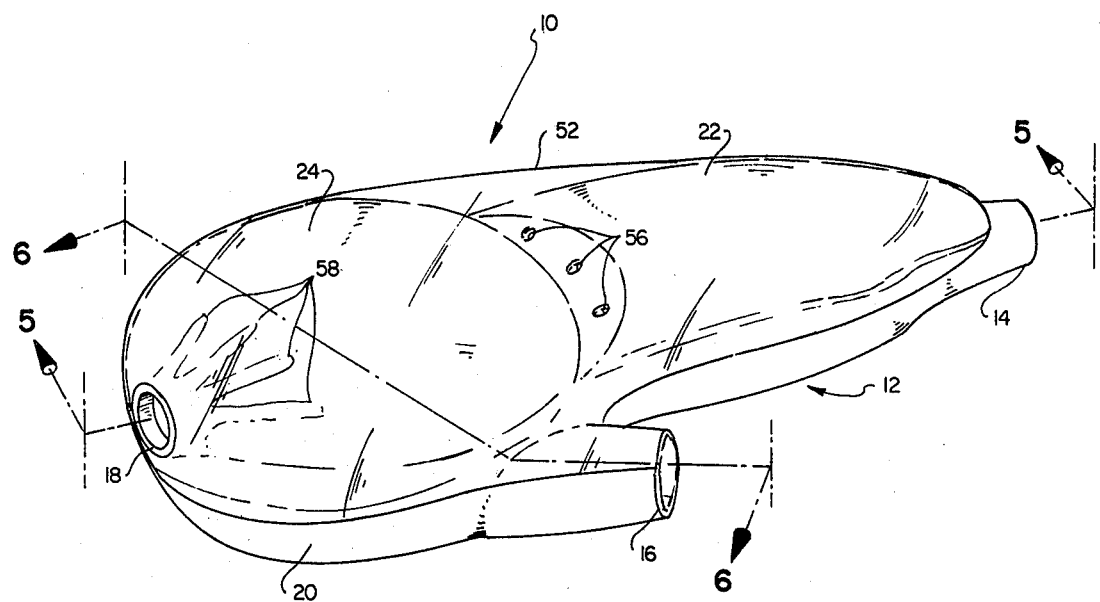
Fig. 1
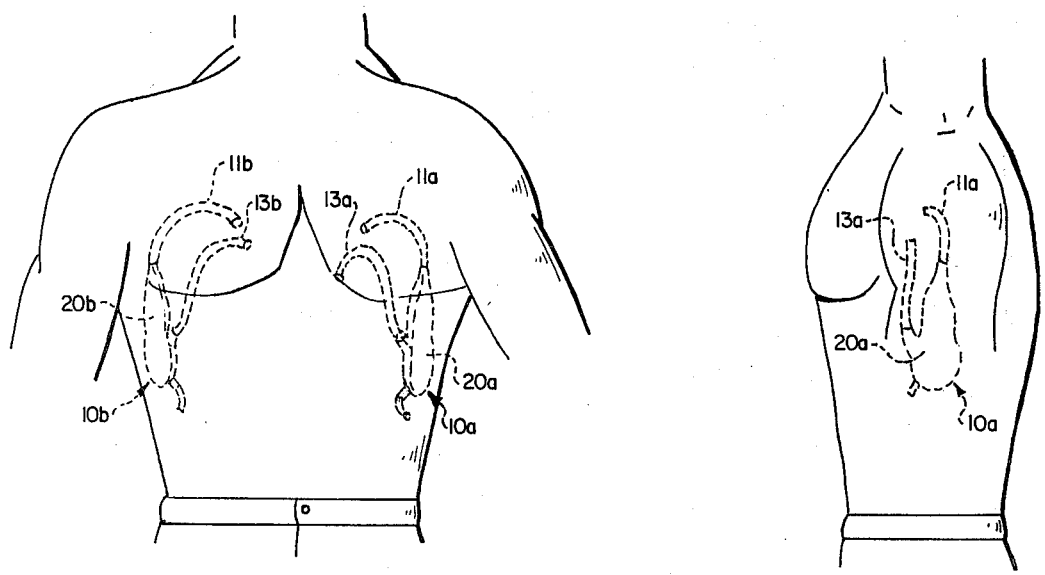
Fig. 2
Fig. 3

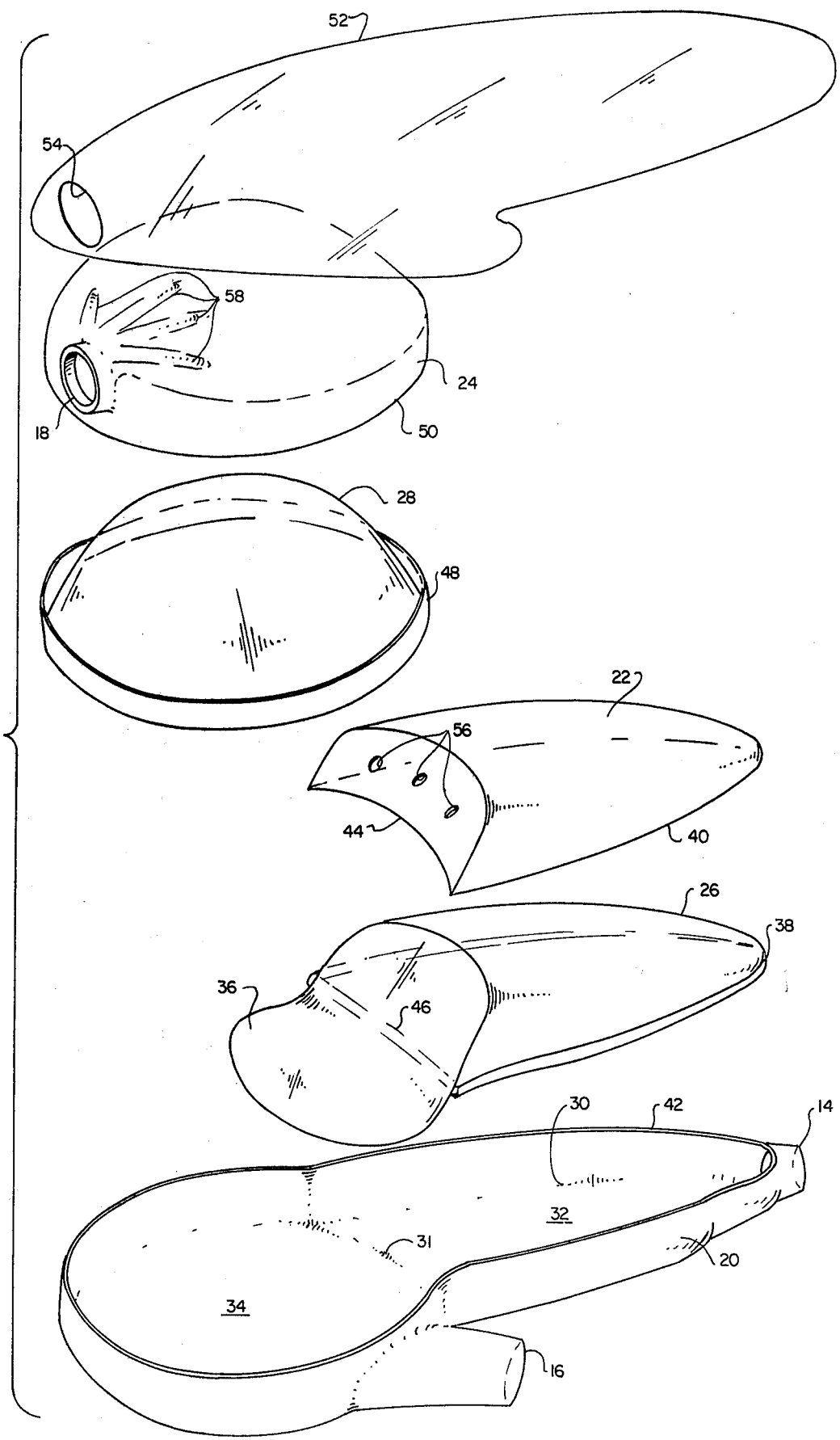

VACUUM

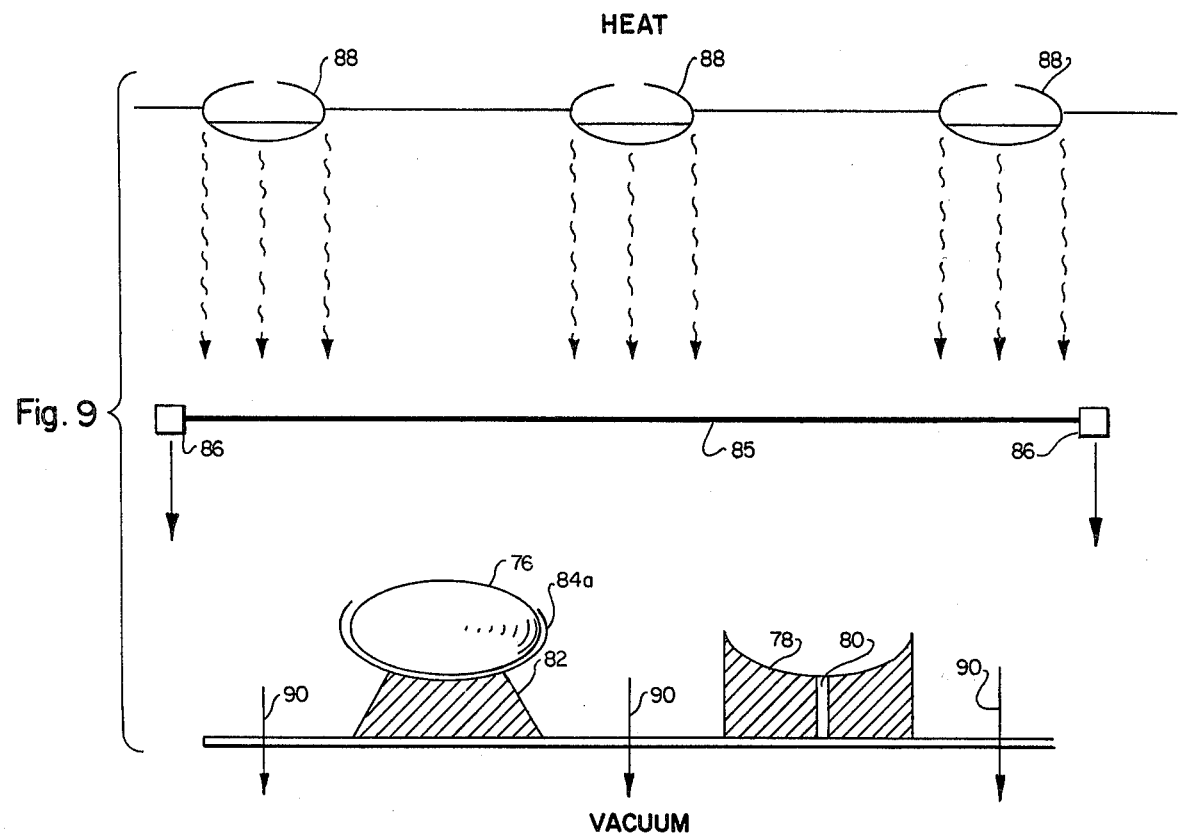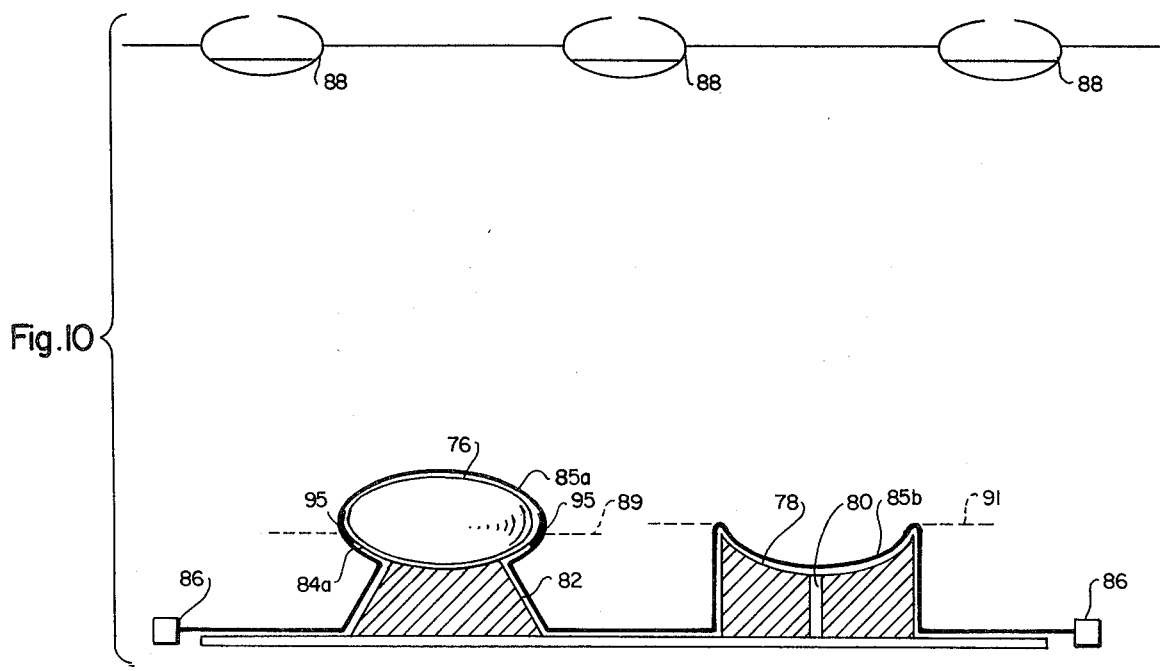

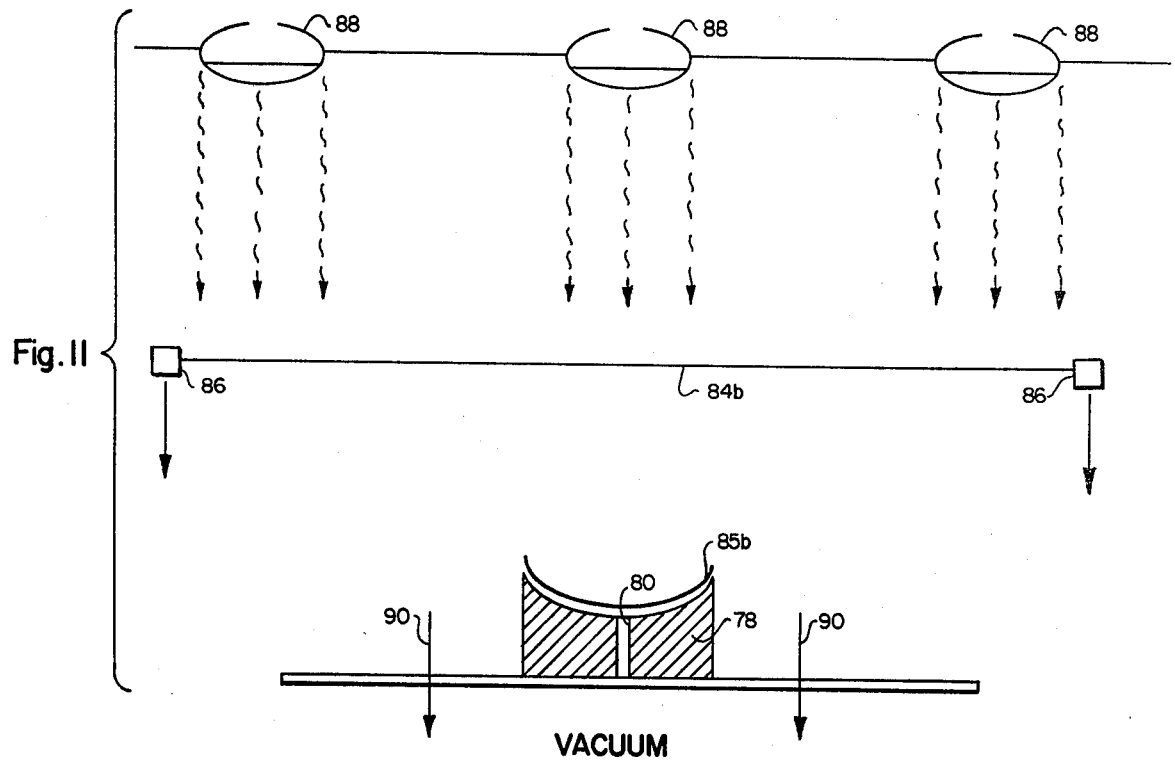
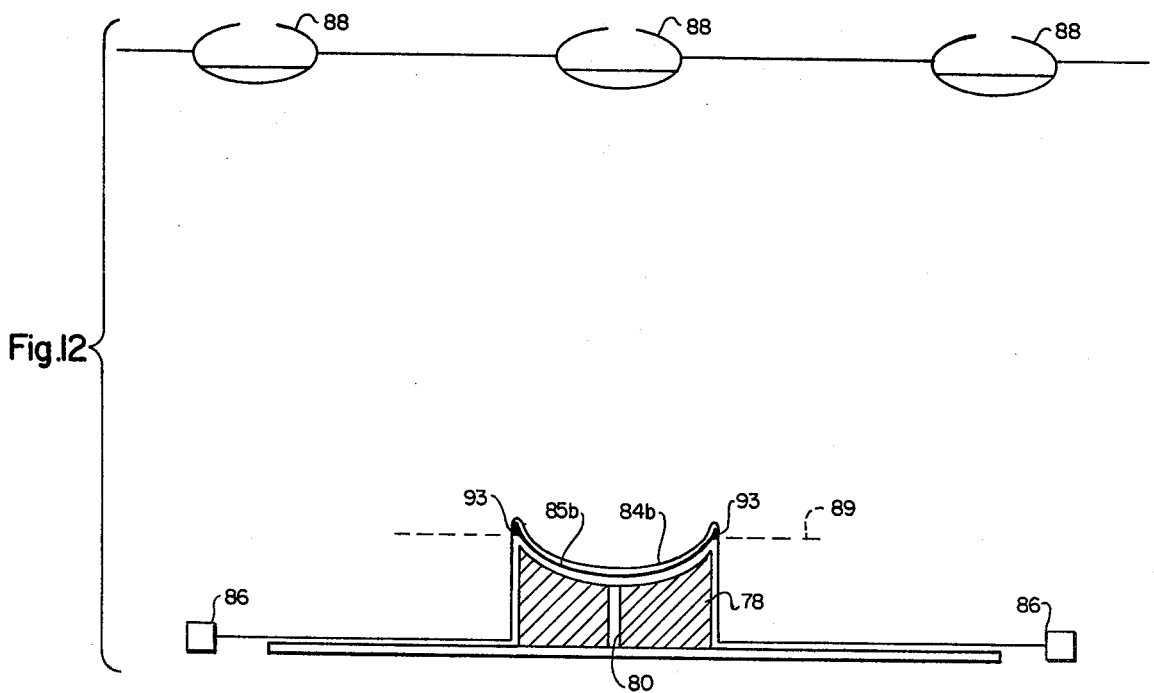

VACUUM

VACUUM MOLDING TECHNIQUE FOR MANUFACTURING A VENTRICULAR ASSIST DEVICE

BACKGROUND

1. Field of the Invention

This invention relates to an artificial heart apparatus, and more particularly, to ventricular assist devices and a method of manufacturing the ventricular assist devices.

2. The Prior Art

Clinical experience has shown that the cardiovascular circulation of patients in severe or even total heart failure can be sustained with proper left ventricular and right ventricular assist devices (hereinafter "LVAD" and "RVAD," respectively). However, when a heart is in severe left ventricular failure and needs support for the left ventricle, there is a good chance that the right ventricle will begin to fail when it has to cope with the increased return from the left ventricle plus the return from the LVAD. A common experience then is that less and less blood returns from the lungs to the left atrium, and the LVAD's and the patient's cardiac output decrease. Only a few people recover after support to the left ventricle. And, when patients are finally weaned off the LVAD, the long term results are still very disappointing. Of the few patients in the world literature who initially survived, most have died after a few weeks or months.

This experience leads to the conclusion that for serious cases of heart failure, one should aim for long term support rather than support limited to hours, days, or weeks. Further, one should be prepared not to just support the left ventricle, but both ventricles. However, presently there are no LVADs and RVADs that fit easily and properly inside the human chest. Typically LVADs have to be used either in the abdominal cavity or outside the chest. Also, as a rule total artificial hearts fit less than ideally inside the chest. Moreover, production methods for artificial hearts or heart assist devices presently in use are time consuming, cumbersome and unduly expensive. Thus, what is needed in the art are ventricular assist devices which overcome the disadvantages that have been experienced with the prior art type devices.

BRIEF SUMMARY AND OBJECTS OF THE INVENTION

The apparatus and method of the present invention consist of a novel ventricular assist device and its method of manufacture. The device includes a housing that contains within it an atrial compliance membrane and a ventricular pumping membrane. The membranes and housing are specially constructed to eliminate seams, ridges and places where thrombi could form. The atrial compliance membrane is also formed with an integral extension that serves as a monocusp mitral valve. The ventricular assist device of the present invention may be constructed and used as either an LVAD or as an RVAD or, when both an LVAD and RVAD are used in combination, as a total artificial heart. The ventricular assist device is shaped in such a fashion that it can be conveniently placed and used outside the chest, against the skin, under the skin, inside the chest but exterior to the pleura, or inside the pleura. The ventricular assist device of the present invention may be shielded by an artificial pericardium and is designed so that it will interfere minimally with pulmonary function. Additionally, the ventricular assist device of the present invention may be constructed using a novel vacuum molding process that is simple, fast, and inexpensive.

It is therefore a primary object of the present invention to provide an improved ventricular assist device that may be used either as an LVAD, an RVAD, or in combination as a total artificial heart.

Another important object of the present invention is to provide a unique vacuum forming process for use in manufacturing artificial hearts and assist devices and which is simple, fast and inexpensive.

Another important object of the present invention is to provide a ventricular assist device that is specially configured so that it can be comfortably used either outside the chest, against the skin, under the skin, inside the chest but exterior to the pleura, or inside the pleura.

Yet another important object of the present invention is to provide a ventricular assist device that is designed so that the interior surface is smooth and essentially seamless in order to minimize the formation of thrombi.

Another object of the present invention is to provide a ventricular assist device wherein the mitral valving mechanism may be formed as an integral extension of the atrial compliance membrane.

Yet another object of the present invention is to provide a ventricular assist device that is designed so that when implanted under the skin or inside the chest of a patient, the blood containing ventricular pumping chamber and the artificial atrium of the device will be oriented towards the outside of the patient so that echocardiography can be conveniently used to visualize movements of the membranes and the valves to assess their function and to detect the presence of any thrombi.

These and other objects and features of the present invention will become more fully apparent from the following description and appended claims taken in conjunction with the accompanying drawings.

BRIEF DESCRIPTION OF THE DRAWINGS

FIG. 1 is a perspective illustration of one presently preferred embodiment of the ventricular assist device of the present invention configurated as an LVAD.

FIGS. 2 and 3 schematically illustrate the placement of an LVAD and RVAD in the chest of a patient.

FIG. 4 is an exploded perspective illustration of the embodiment of FIG. 1.

FIGS. 7 through 14 schematically illustrate one presently preferred method of manufacturing an artificial ventricle in accordance with the method of present invention.

DETAILED DESCRIPTION OF THE PREFERRED EMBODIMENTS

Figure 5A:
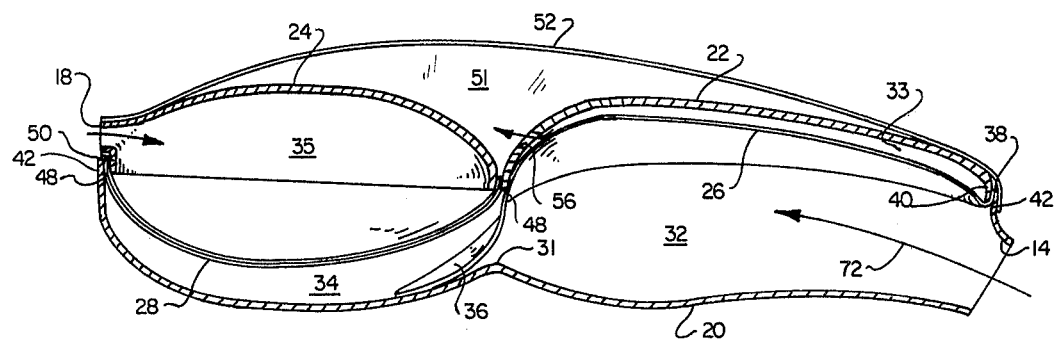
FIG. 5A is a longitudinal cross-sectional view taken along line 5—5 of FIG. 1, and illustrates the position of the ventricular pumping membrane and atrial compliance membrane during the systolic phase of the device.

Reference is next made to the drawings wherein like parts are designated with like numerals throughout.

1. The Apparatus

One presently preferred embodiment of the ventricular assist device of the present invention is generally indicated at 10 in FIG. 1. The ventricular assist device illustrated in FIG. 1 is configured as an LVAD although it will of course be appreciated that the ventricular assist device of this invention can be used either as an LVAD or an RVAD, or in combination as a total artificial heart.

When used to assist the natural heart (not shown), the LVAD 10a and RVAD 10b (see FIG. 2) are connected to the natural heart via tubes 11 and 13. On the left side, blood is sucked from the left ventricle or from the left atrium possibly, but not necessarily, via the superior pulmonary vein (not shown) and through the tube 11a. The blood is returned from LVAD 10a through tube 13a to the ascending aorta (not shown). On the right side, the blood may be taken from the right artrium only, or, if desired, also from the right ventricle through tube 11b. Blood is returned from RVAD 10b through tube 13b to the pulmonary artery. Thus, LVAD 10a controls or assists systemic circulation, while RVAD 10b controls or assists pulmonary circulation.

With further reference to FIGS. 1 through 3, it will be seen that the ventricular assist device of this invention has an exterior shape that is gently curved and which is generally flat. Thus, unlike the prior art type ventricular assist devices or total artificial hearts currently in use, the ventricular assist device of the present invention can be conveniently implanted under the skin, inside the chest but exterior to the pleura, or inside the pleura. The unique size and flat, contoured shape of the ventricular assist device 10 avoids crowding of adjacent organs and accommodates implantation within the available anatomical space as generally illustrated in FIGS. 2 and 3. This is a significant advantage since it makes the ventricular assist device much more comfortable and convenient, and thus enhances the ability of the device to be used for purposes of providing long-term support. In contrast, the prior art type devices are much larger and must typically be worn outside of the patient or inside the abdominal cavity.

With further reference to FIG. 1, the ventricular assist device 10 includes a housing generally designated 12. Housing 12 includes an inlet port 14 through which blood is admitted into the housing and an outlet port 16 through which the blood is expelled as it is pumped. Housing 12 also includes a port 18 through which a driving fluid is pumped into and out of the ventricular pumping chamber as hereinafter more fully described. Port 18 is connected through tubing (not shown) to a conventional pump (not shown), while ports 14 and 16 are connected through tubing to the appropriate arteries, atria or veins of the patient as described above.

As shown best in FIG. 4, housing 12 is formed in three parts which include the blood side of the housing indicated at 20, an atrium cover indicated at 22 and a ventricle cover indicated at 24. The interior surface 30 of the blood side 20 of housing 12 is constructed so that it is gently curved and presents a smooth surface. Additionally, the internal seams formed at the junctures between the pumping membrane 28, the atrial compliance membrane 26 and blood side portion 20 of housing 12 may be rendered smooth and essentially seamless by applying a solution containing a suitable elastomer such as polyurethane to each of the seams. This can be done by applying the solution to the inner seam through a syringe with a long cannula, or by covering the entire intima with an air-dried surface of polyurethane by using a rotational cavity molding process. Advantageously, this helps to prevent the formation of thrombi as blood flows into and is pumped out of the housing.

The blood side 20 of housing 12 is shaped so as to provide an elongated atrial blood chamber 32 which communicates with a generally circular shaped ventricular blood chamber 34. The atrial and ventricular blood chambers 32 and 34 formed in the blood side portion 20 of housing 12 are separated by a slight ridge 31 (see also FIGS. 5A and 5B).

A compliance membrane 26 is sealed between the atrium cover 22 and the blood side portion 20 of housing 12 which forms the atrial blood chamber 32. As hereinafter more fully described, the edge 38 of compliance membrane 26 is vacuum formed such that it is folded over and is bonded to the corresponding edge 40 (see also FIGS. 5A and 5B) of the atrium cover 22.

A one-way flap valve 36 is formed as an integral extension of the atrial compliance membrane 26. Flap valve 36 functions as a monocusp mitral valve which controls the flow of blood from the atrial blood chamber 32 (see FIGS 5A and 5B) to the ventricular blood chamber 34. The one-way flap valve 36 is bonded to the curved edge 44 of the atrium cover 22 along a corresponding portion 46 of the flap valve 36. Thus, a fluid tight seal is formed between the atrium cover 22 and blood side portion 20 of housing 12 at the periphery of the compliance membrane 26. In this manner the atrial compliance chamber that is formed in the space 33 (see FIGS. 5A and 5B) between the atrium cover 22 and compliance membrane 26 is completely sealed and is fluid tight with respect to the atrial blood chamber that is formed in the space 32 between the compliance membrane 26 and blood side portion 20 of housing 12.

Figure 5B:
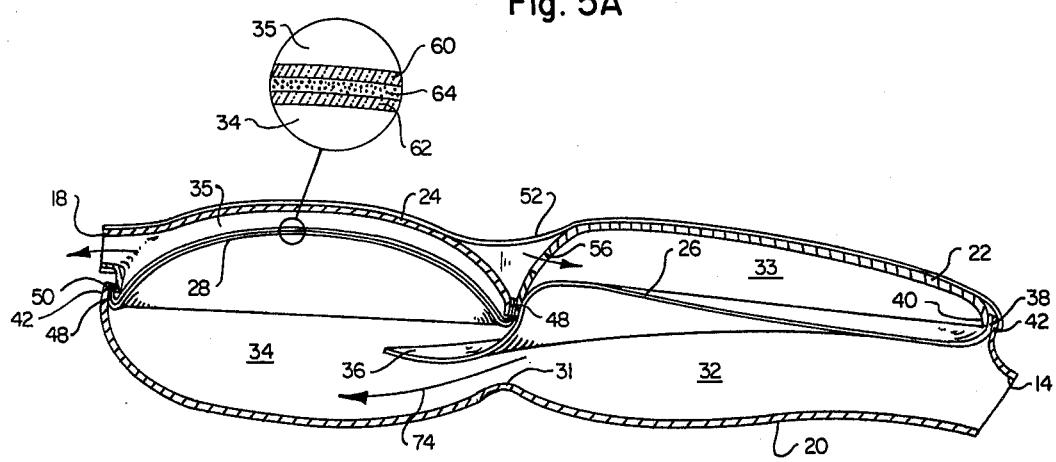
FIG. 5B is a longitudinal cross-sectional view taken along line 5—5 of FIG. 1, and illustrates the ventricular pumping membrane and atrial compliance membrane during the diastolic phase of the device's operation.

In like fashion, a ventricular pumping membrane 28 is sealed between the ventricle cover 24 and blood side portion 20 of housing 12 that forms the ventricular blood chamber 34. The ventricular pumping membrane 28 is also vacuum formed such that its edge 48 folds over and is bonded to the corresponding edge 50 of the ventricle cover 24. As best illustrated in FIGS. 5A and 5B, a portion of the edge 48 of ventricular pumping membrane 28 is also bonded between the ventricle cover 24 and atrium cover 22. Thus, the ventricular pumping membrane 28 provides a fluid tight seal at its periphery which separates the drive fluid pumping chamber 35 (see FIGS. 5A-6B) formed between the ventricle cover 24 and ventricular pumping membrane 28 from the ventricular blood chamber 34 that is formed between the ventricular pumping membrane 28 and blood side portion 20 of housing 12.

As illustrated in the enlarged insert of FIG. 5B, the ventricular pumping membrane 28 may be constructed as a double layer pumping membrane which includes two layers of elastomers 60 and 62 separated by a lubricant layer 64. The elastomers may be polyurethane, polyethylene or other similar kinds of blood compatible elastomers, while the lubricant may be graphite. The graphite layer 64 permits the elastomeric layers 60 and 62 to slide freely relative to each other. This multi-layered configuration of pumping membrane 28 provides greatly increased durability and safety, while preserving the necessary flexibility. Other, additional layers of elastomeric material could also be provided, and the compliance membrane 26 may also be constructed as a multi-layered membrane if desired.

A plurality of divergent fluid channels 58 (see FIG. 4) are formed on the interior surface of the ventricle cover 24. The divergent fluid channels 58 fan outwardly from the port 18 to provide a distribution system for evenly dispersing the drive fluid admitted through the port 18 into the ventricular pumping chamber 35. As hereinafter more fully described, as the drive fluid is alternately pumped into the ventricular blood chamber 35 and then withdrawn, the membrane 28 will expand and then retract, causing the blood to be pumped from the ventricular blood chamber 34.

Figure 6B:
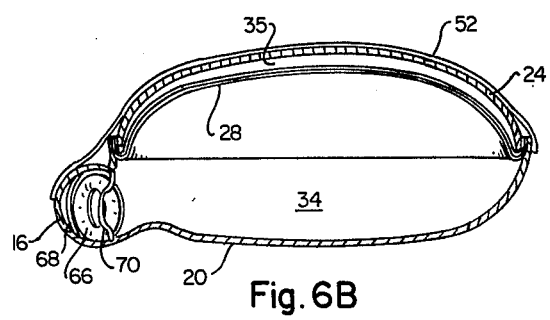
FIG. 6B is a cross-sectional view taken along line 6—6 of FIG. 1, and illustrates the arterial valve mechanism and ventricular pumping membrane during the diastolic phase of the device's operation.
Figure 6A:
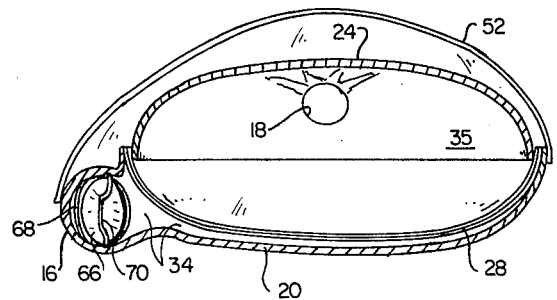
FIG. 6A is a cross-sectional view taken along line 6—6 of FIG. 1, and illustrates the ventricular pumping membrane and arterial valve mechanism during the systolic phase of the device's operation.

As shown in FIGS. 6A and 6B, blood pumped from the ventricular blood chamber 34 is controlled by an arterial valve mechanism positioned in the outlet port 16. The arterial valve mechanism is a conventional heart valve which consists of a small disc 66 supported between two offset bars 68 and 70. The disc 66 is normally in a closed position (see FIG. 6B) while blood fills the ventricular blood chamber 34 during diastole, and is changed to the open position (see FIG. 6A) as blood is pumped through the outlet port 16 during systole. The arterial valve mechanism may be separately constructed so that it can be attached to the device at the time of surgical implantation, in accordance with well-known surgical techniques.

With continued reference to FIG. 4, a thin, flacid membrane 52 is provided which corresponds in its general size and shape to the upper portion of the housing 12 formed by the ventricle cover 24 and atrium cover 22. The membrane 52 is provided with a hole 54 at one end which fits over the port 18 of ventricle cover 24. The membrane 52 is bonded along the edge 42 of the blood side portion 20 of housing 12 so as to form a fluid tight seal. Membrane 52 serves as an artifical pericardium that encloses gaseous fluid which is alternately admitted and expelled from the atrial compliance chamber 33 (see FIG. 5B) through the holes 56 provided in the atrium cover 22. When an LVAD and RVAD are used together (see FIG. 2) the cavities of the artificial pericardium of each device may be interconnected to provide a larger compliance volume and to take advantage of alternate pulsation of the LVAD and RVAD, which greatly reduces the need of such volume. The artificial pericardium formed by membrane 52 also provides a smooth outer surface which fits comfortably under the skin or inside the chest of a patient.

The artificial pericardium formed by membrane 52, as well as the ventricle cover 24, atrium cover 22, blood side portion 20 of housing 12 and membranes 26 and 28 may be formed from biocompatible elastomers, in accordance with the method hereinafter more fully described. The inside surfaces of the ventricular assist device which come into contact with blood can be coated with a biolized layer consisting of porous polyurethane filled for example with cross-linked gelatin, or they may be treated with Heparin, prostaglindin or other anticoagulants. The outside surfaces of the device 10 can be coated with antibiotics such as Gentamycin.

The operation of the ventricular-assist device of the present invention is best understood with reference to FIGS. 5A–6B. With reference first to FIG. 5A, as schematically represented by the arrow 72, blood enters the ventricular-assist device through the inlet port 14 and begins to fill the atrial blood chamber 32. As the atrial blood chamber 32 is filled with blood, the atrial compliance membrane 26 expands, forcing the gaseous fluid contained in the atrial compliance chamber 33 out of the atrial compliance chamber 33 through the holes 56 contained in the atrium cover 22. The gaseous fluid from the atrial compliance chamber 33 fills the space 51 that is enclosed by the thin, flacid membrane 52 causing the membrane 52 to expand.

At the same time as blood is filling the atrial blood chamber 32, a drive fluid, which may be either gaseous or liquid, is pumped into the ventricular pumping chamber 35 causing the ventricular pumping membrane 28 to expand and expel the blood that is contained in the ventricular blood chamber 34 through the outlet port 16 and arterial valve mechanism 66 (see also FIG. 6A). As the ventricular pumping membrane 28 expands and expels the blood from the ventricular blood chamber 34, the pressure exerted on the blood contained in the ventricular blood chamber 34 maintains the one-way flap valve 36 of the atrial compliance membrane 26 in the closed position, as illustrated in FIG. 5A. This sequence of the device's operation is referred to as the systolic phase of the device's operation since blood is expelled from the ventricular-assist device by the pumping membrane 28 during this portion of the device's operation.

The second or diastolic phase of the devices's operation is illustrated in FIGS. 5B and 6B. As shown in those figures, after blood has been expelled from the ventricular blood chamber 34, the drive fluid is withdrawn by the pumping mechanism (not shown) through the port 18. As the drive fluid is withdrawn through port 18, the ventricular pumping membrane 28 is pulled upwardly. This releases the fluidic pressure holding the one-way flap valve 36 in the closed position so that the valve 36 may then be opened as illustrated in FIG. 5B. As the one-way flap valve 36 is opened, blood flows from the atrial blood chamber 32 past the one-way flap valve 36 and into the ventricular blood chamber 34, as schematically illustrated by the arrow 74. As the blood flows from the atrial blood chamber 32 and fills the ventricular blood chamber 34, the gaseous fluid contained in the space 51 flows through the ports 56 of atrium cover 22 and fills the atrial compliance chamber 33. The disc 66 of the atrial valve mechanism (FIG. 6B) remains closed until the ventricular blood chamber 34 is completely filled with blood at which time the systolic phase begins again and the drive fluid is then pumped back into the ventricular pumping chamber 35 causing the pumping membrane 28 to expel the blood in the manner previously described.

Advantageously, as shown in FIG. 5A, the one-way flap valve 36 is formed as an integral extension of the atrial compliance membrane 26. Flap valve 36 also is gently curved so that it conforms to the contour of ventricular blood chamber 34. Thus, during the systolic phase of the device's operation, the ventricular side of the flap valve 36 is continually washed by the motion of the blood within the ventricular blood chamber 34. This helps to prevent the formation of thrombi in and around the valve 36.

A further significant advantage of the ventricular-assist device of the present invention is that the ventricular blood chamber 34 and atrial blood chamber 32 are located on the same side of the housing. Thus, when the device is placed in a patient such as illustrated in FIGS.

2 and 3, the blood side portion 20 of the housing 12 faces outwardly. And since the ventricular pumping chamber 35 and atrial compliance chamber 33 are located on the opposite side of the housing and are oriented so that they face inwardly with respect to the patient, neither the ventricular pumping chamber 35 nor the atrial compliance chamber 33 will interfere with ultrasound waves passing through the blood side portion 20 of the device when using echocardiography to take pictures of the device after it has been implanted.

2. The Method of Manufacture

The ventricular assist device of the present invention may be constructed using a novel vacuum-molding process that is simple, fast and inexpensive. By way of background, vacuum-molding involves a process in which a sheet or layer of thermoplastic polymer or elastomer material is heated until it becomes very soft and malleable. The soft layer of thermoplastic is then lowered over a mold and a vacuum is created under the mold which sucks the elastomer tightly over the top of the mold. In this way, the thermoplastic material is formed by the mold. Mechanical help, for example by pressing the top of the vacuum-formed thermoplastic layer with a wooden form, may be used to smooth the vacuum-formed layer of thermoplastic and this is sometimes advantageous.

Using this technique, a vacuum formed print made over a convex mold will have an exact inner dimension. A vacuum formed print made over a concave mold will have an exact outer dimension. Thus, one can predict an exact fit between the prints vacuum formed over convex and concave molds when the molds themselves are fitted, which can easily be done by casting one mold inside the other.

The general principles described above may be used in connection with one presently preferred method of the present invention, as schematically illustrated in FIGS. 7-14. For purposes of simplifying the drawing and description, FIGS. 7-14 schematically represent the steps for manufacturing an artificial ventricle, including a ventricular blood chamber and a drive fluid pumping chamber that are separated by a ventricular pumping membrane sealed within a housing, as hereinafter more fully described. It will of course be appreciated that the same general technique used to construct the artificial ventricle of FIG. 14 may also be employed to construct a complete LVAD or RVAD in accordance with the embodiment of the present invention illustrated in FIG. 4, as hereinafter described.

Figure 7:
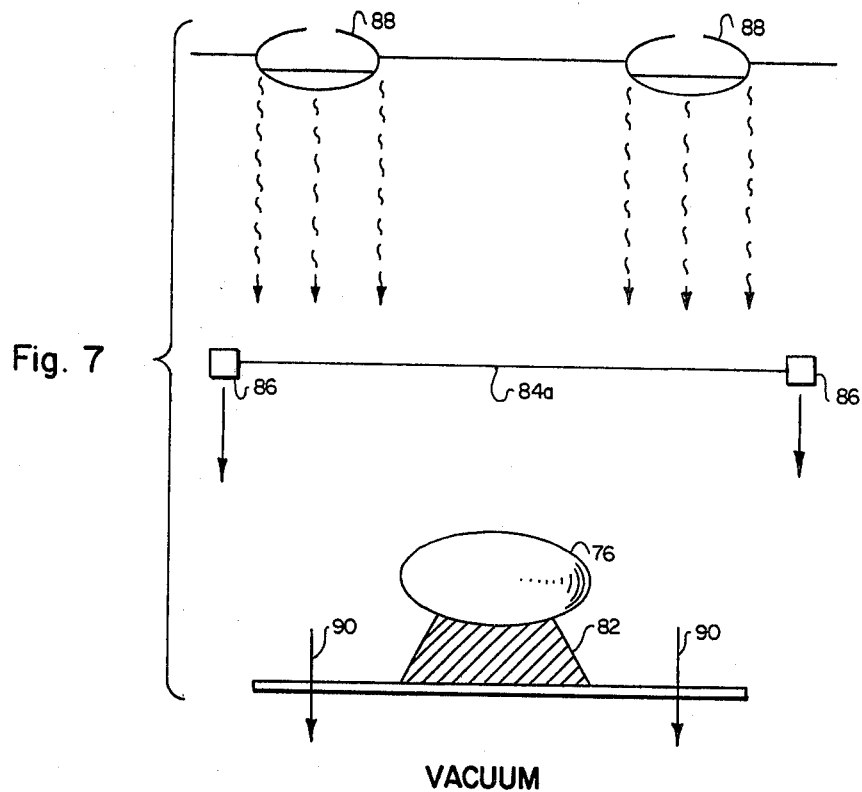
Figure 8:
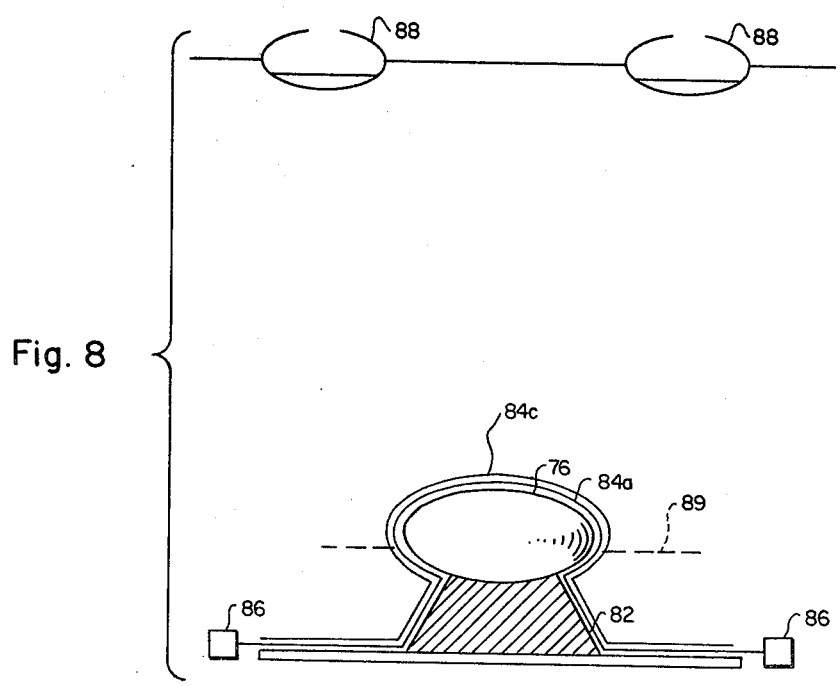

As illustrated in FIGS. 7 and 8, a convex mold 76 is first prepared having the desired shape of the artifical ventrical. The convex mold 76 is supported on a pedestal 82 to insure that the vacuum formed thermoplastic will cover the greatest circumference of the mold 76. A thin layer of thermoplastic polymer or elastomer 84a is supported at its ends as at 86 and is suspended over the top of the mold 76. A source of heat 88 is then energized so that the layer 84a of thermoplastic becomes soft and malleable. As schematically represented by the arrows 90, a vacuum is then applied beneath the mold 76 so that the layer 84a of thermoplastic is sucked down onto the top of the mold as illustrated best in FIG. 8. After the layer 84a of thermoplastic cools, it is cut at the line indicated at 89. Layer 84a forms one of the thin layers of the double layer ventricular pumping membrane, as more fully described below.

The steps of the process illustrated in FIGS. 7 and 8 are repeated so that an extra layer of polyethelene 84c of the same thickness as layer 84a is vacuum formed over the convex mold 76 and layer 84a. Layer 84c, which will later be removed, simulates the thickness of that part of pumping membrane 84b (see FIG. 11) that will attach to the concave drive chamber 85b. From the convex mold 76, a concave mold 78 is formed which corresponds to the thickness of the convex mold 76, including the thin layers 84a and 84c of polyethelene. Mold 78 is provided with a small bore 80 which eliminates entrapment of air when the thermoplastic is vacuum formed over the concave mold 78.

Next, as shown in FIG. 9, layer 84c is removed and the mold 76 is turned over. A somewhat thicker layer 85 of thermoplastic is then heated and vacuum formed over molds 76 and 78. The layer 85 of thermoplastic is then cut (see FIG. 10) at the lines indicated at 89 and 91. The portion 85a of thermoplastic vacuum formed over mold 76 and the portion 85b of thermoplastic vacuum formed over mold 78 form the ventricular blood chamber and drive fluid pumping chamber portions of the housing or shell of the artificial ventricle. The portion 85a of the artificial ventricle vacuum formed over convex mold 76 will have an outer dimension that will exactly fit the inner dimension of the portion 85b of the artificial ventricle vacuum formed over the concave mold 78 even when the portion 84b (see FIG. 11) of the pumping membrane is in place, due to the extra layer 84c of polyethelene that is removed.

As shown in FIGS. 11 and 12, a second thin layer 84b of thermoplastic is next vacuum formed directly onto the layer 85b. Layer 84b forms the other thin layer of the double pumping membrane. It will of course be appreciated that layers 84a and 84b may be different types of polymers if desired.

The thin layer of thermoplastic 84a vacuum formed over convex mold 76 is bonded around its periphery as at 95 (see FIG. 10) to the inside surface of the layer of theromplastic 85a. Similarly, the thin layer of thermoplastic 84b vacuum formed over the concave mold 78 (see FIG. 12) is bonded around its periphery at 93 to the outer surface of the edge of the layer 85b. The bonding may be achieved by using a glue, a solvent, by heat sealing, or by ultrasonic welding. The thin layer of thermoplastic 84a vacuum formed over the convex mold 76 forms the blood side of the double pumping membrane and the thin layer 84b vacuum formed over the concave mold 78 forms the drive fluid or air side of the double pumping membrane.

Figure 13:
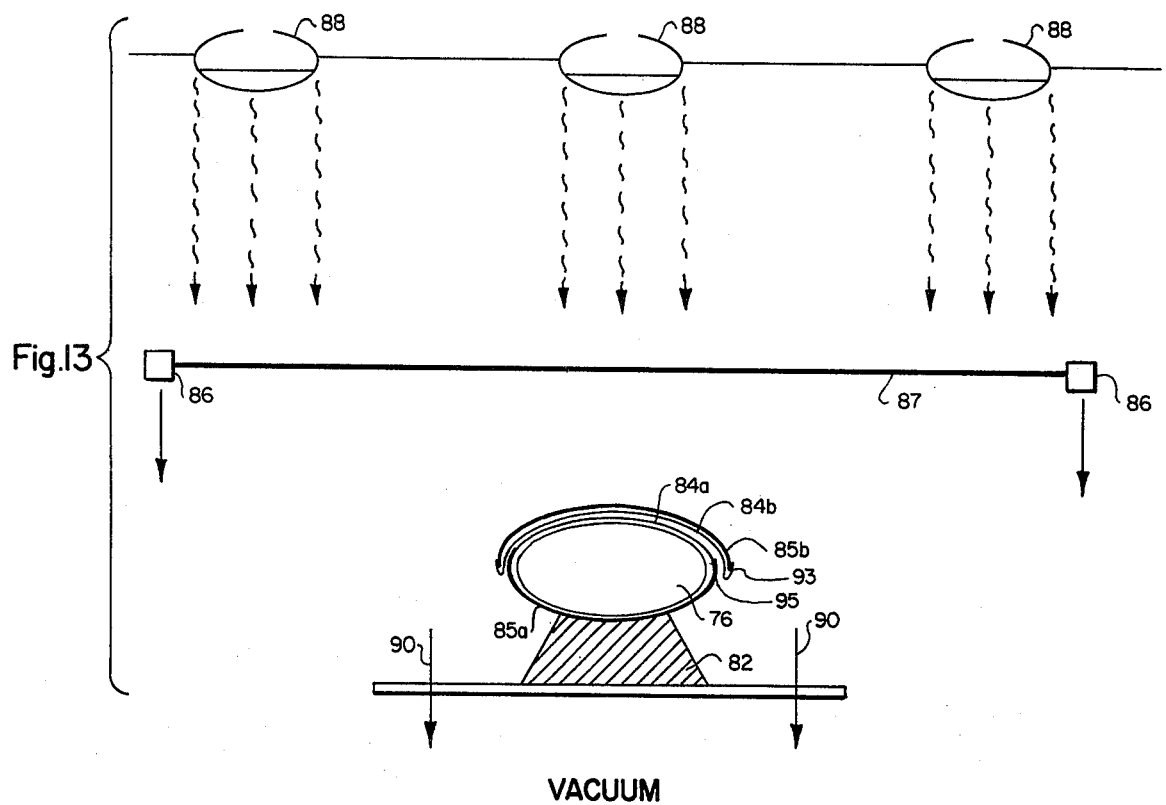
Figure 14:
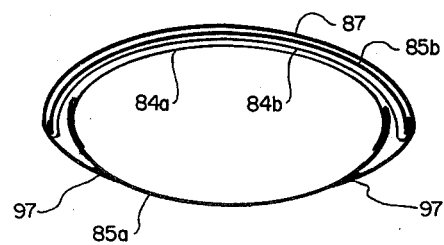

After the layer of thermoplastic 84b is cut along line 89 (see FIG. 12) the drive fluid pumping chamber portion of the artificial ventricle formed by the layers 85b and 84b is removed from the concave mold 78 and is placed on top of the ventricular blood chamber portion of the artificial ventricle vacuum-formed over the convex mold 76, as illustrated in FIG. 13. The two portions of the artificial ventricle are brought together such that the thin layers of thermoplastic 84a and 84b are assembled together to form a double layer pumping membrane. The two layers of thermoplastic 84a and 84b may be separated by a layer of lubricant such as graphite.

Another, thicker layer 87 of thermoplastic polymer is then suspended over the top of the two portions of the artificial ventricle assembled together and is heated and vacuum formed over the top of the assembly. The layer 87 of thermoplastic is then cut and bonded at 97 (see FIG. 14) to the periphery of thermoplastic layer 85a so as to form a completely enclosed artificial ventricle which includes a ventricular blood chamber and a drive fluid pumping chamber separated by a double layer pumping membrane. The double layer pumping membrane is formed by the two relatively thin layers of thermoplastic 84a and 84b which are separated by a graphite or other lubricant. The housing of the artificial ventricle is formed by the layers 85a and 85b which are in turn joined together by the outer layer 87 of thermoplastic.

The mold 76 is constructed from a material that can be easily melted, dissolved or broken to permit removal of the mold through the inlet and outlet ports (not shown) of the artificial ventricle after it has been completely formed. Such materials include certain silicones, Wood's metal, wax, polyethylene or ice. Once the mold 76 has been melted, dissolved or broken and removed through the inlet or outlet ports of the artificial ventricle, the inner seams within the ventricular blood chamber can be essentially eliminated by applying a solution containing polyurethane through a long, thin cannula attached to a syringe. The cannula may be inserted through either the inlet or the outlet ports (not shown) of the artificial ventricle similar to the manner described above in connection with FIG. 4. In the alternative, the entire intima of the ventricular blood chamber may be covered with an air-dried surface of polyurethane using a rotational cavity molding process.

In accordance with the general principles schematically illustrated in connection with FIGS. 7-14, the embodiment of the ventricular assist device of the present invention illustrated in FIG. 4 can be simply and economically manufactured. Convex molds are first prepared having the shape of the housing 12 which is defined by the blood side portion 20 of the housing, the ventricle cover 24 and atrium cover 22. Using the convex molds prepared for each of these parts, a first layer of thermoplastic polymer is vacuum formed over the convex molds in the manner previously described. The first layer of thermoplastic is then cut to form the blood side portion 20, atrium cover 22 and ventricle cover 24 of the housing 12. In this manner, a complete housing is vacuum formed, including the inlet and outlet ports 14 and 16, and the port 18 through which drive fluid is pumped into and out of the ventricular pumping chamber.

Using the convex molds that were used to form the ventricle cover 24 and atrium cover 22, concave molds are formed corresponding to each of the convex molds. A thin layer of thermoplastic polymer is then vacuum formed over the concave molds to form the first layer of the ventricular pumping membrane 28 and atrial compliance membrane 26. This layer of thermoplastic is then coated with a lubricant such as graphite, except at its peripheral edges. A second thin layer of thermoplastic is vacuum formed over the convex mold and is bonded at its periphery to the first layer in order to form a double layer pumping membrane such as previously described in connection with FIG. 5B. It will, of course, be appreciated that additional layers may be formed over any convex mold if it is desired to have more than two layers for the ventricular pumping membrane 28 or atrial compliance membrane 26.

When the atrial compliance membrane 26 and ventricular pumping membrane 28 are cut and removed from the concave molds, each of the membranes 28 and 26 will have a peripheral edge 48 and 38, respectively, that is folded over and which may be bonded to the peripheral edge 50 and 40 of the ventricle cover 24 and atrium cover 22.

Rather than using the concave molds, the membranes 26 and 28 may be vacuum formed directly onto the atrium cover 22 and ventricle cover 24. For example, to vacuum form the ventricular pumping membrane 28 directly onto the ventricle cover 24, the ventricle cover 24 is turned over and is supported on a pedestal so that the peripheral edge 50 of the ventricle cover 24 extends slightly beyond the edge of the supporting pedestal. The first thin layer of thermoplastic polymer is then vacuum formed directly onto the concave interior surface of the ventricle cover 24. The first thin layer of thermoplastic is then coated with graphite lubricant as described above. The periphery of the ventricular pumping membrane 28 will be vacuum formed over the edge 50 of the ventricle cover 24 and may be bonded thereto to form a fluid tight seal about the entire periphery of the ventricle cover 24. If a double layer pumping membrane is desired, the second thin layer of thermoplastic may be vacuum formed over a corresponding convex mold.

In like manner, the atrium cover 22 may be turned over and supported on a pedestal such that the edges 40 and 44 of the atrium cover will be slightly exposed and the layer of thermoplastic used to form the atrial compliance member 26 may then be vacuum formed directly onto the concave interior surface of the atrium cover 22.

Once the blood side portion 20, atrium cover 22 and ventricle cover 24 of the housing and the membranes 26 and 28 have each been vacuum formed, assembled and bonded at the periphery to form a fluid tight ventricular assist device, the thin flacid membrane 52 may then be vacuum-formed over the ventricle cover 24 and atrium cover 22 to form the articifial pericardium of the device.

As previously indicated, interior seams formed along the peripheral edges of the membranes 26 and 28 can be smoothed by applying a polyurethane in solution to the seams through a long thin cannula introduced through any of the ports 14 or 16. In the alternative, the entire intima or interior surface of the atrial and ventricular blood chambers can be coated with an air-dried surface of polyurethane using a rotational cavity molding process, as is well-known in the art.

It will be appreciated that the thickness of the layers of thermoplastic polymer used for the housing 12 and the membranes 26 and 28 are a matter of design choice. It is desirable that the housing 12 be thick enough to adequately protect the membranes 26 and 28 from puncture or damage, whereas the membranes 26 and 28 must be more thin so that they can be easily flexed for purposes of the operation of the device as it pumps blood.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of manufacturing an artificial ventricle which comprises a housing and a pumping membrane which divides the interior of said housing into a ventricular blood chamber and a drive fluid pumping chamber, the method comprising the steps of:
  (a) preparing a convex mold having the same shape as the desired artificial ventricle;
  (b) vacuum forming a thin layer of thermoplastic polymer over a portion of a first side of said mold;
  (c) turning the mold over and vacuum forming a thick layer of thermoplastic polymer over said mold so as to form the ventricular blood chamber portion of the artificial ventricle;
  (d) vacuum forming a second thicker layer of thermoplastic so as to form the drive fluid pumping chamber portion of said housing on a second side of said mold;
  (e) supporting the portion of said housing vacuum formed in step (d) on a pedestal and vacuum forming a thin layer of thermoplastic polymer onto said portion of the housing so as to form the drive fluid pumping chamber of said artificial ventricle;
  (f) assembling together the thin layers of thermoplastic polymer vacuum formed in steps (b) and (e) so as to form a double layer pumping membrane;
  (g) vacuum forming a third, thicker layer of thermoplastic polymer which fits over the assembly of step (f);
  (h) bonding the periphery of the thermoplastic layer vacuum formed in step (g) to the periphery of the thermoplastic layer vacuum formed in step (d) so as to enclose the ventricular blood chamber and drive fluid pumping chamber formed in steps (c) and (e) in a housing; and
  (i) removing the convex mold used to form the ventricular blood chamber in step (c).

2. A method as defined in claim 1, further comprising the step of placing a layer of graphite between the thin layers of thermoplastic prior to assembling them in step (f).

3. A method as defined in claim 1, further comprising the steps of:
  bonding the periphery of the thin layer of thermoplastic formed in step (b) to the inside periphery of the layer of thermoplastic vacuum formed in step (c); and
  bonding the periphery of the thin layer of thermoplastic formed in step (e) to the outside periphery of the layer of thermoplastic vacuum formed in step (d).

4. A method of manufacturing a ventricular blood chamber for use in an artificial ventricle, said blood chamber comprising a shell having a flexible pumping membrane vacuum formed onto said sheel, and the method comprising the steps of:
  (a) preparing a convex mold having the same shape as the desired artificial ventricle;
  (b) heating a thin layer of thermoplastic polymer until it becomes malleable;
  (c) vacuum forming said flexible pumping membrane by placing the heated layer of step (b) over the convex mold of step (a) and applying a vacuum;
  (d) turning the convex mold over;
  (e) heating a second, thicker layer of thermoplastic polymer until it becomes malleable, said second layer of thermoplastic polymer being used as said shell;
  (f) vacuum forming said flexible pumping membrane onto said shell by placing the heated layer of step (e) over the convex mold and applying a vacuum; and
  (g) removing the convex mold.

5. A method as defined in claim 4, wherein steps (b) and (c) are repeated one or more times to form a pumping membrane comprising several different layers.

6. A method as defined in claim 5, wherein each said layer is a different type of polymer.

7. A method as defined in claim 5, further comprising the step of treating essentially all but the peripheral portion of the outer surface of each said layer used to form said pumping membrane with a lubricant prior to vacuum forming the next layer.

8. A method as defined in claim 4, further comprising the step of bonding the periphery of said thin layer of thermoplastic to the interior wall of the second thermoplastic layer vacuum-formed in step (f) by applying a bonding agent to the periphery of said thin layer prior to step (f).

9. A method as defined in claim 4, further comprising the step of bonding the periphery of said thin layer of thermoplastic to the interior wall of the second thermoplastic layer vacuum formed in step (f) by heat sealing said periphery to said interior wall.

10. A method as defined in claim 4, further comprising the step of bonding the periphery of said thin layer of thermoplastic to the interior wall of the second thermoplastic layer vacuum formed in step (f) by ultrasonically welding said periphery to said interior wall.

11. A method as defined in claim 4, further comprising the step of smoothing the inner seam formed at the juncture of said layers of thermoplastic by applying an elastomer or polyurethane in solution to said inner seam.

12. A method as defined in claim 4, further comprising the step of smoothing the inner seam formed at the juncture of said layers of thermoplastic by rotational cavity molding the interior walls of said ventricular blood chamber with an air dried surface of polyurethane.

13. A method as defined in claim 4, wherein said mold is made from material that can be melted, dissolved or broken to permit removal of the material.

14. A method as defined in claim 13, wherein step (g) comprises the step of melting said mold.

15. A method as defined in claim 13, wherein step (g) comprises the step of dissolving said mold.

16. A method as defined in claim 13, wherein step (g) comprises the step of breaking said mold into small pieces.

17. A method of manufacturing a drive fluid pumping chamber for use in an artificial ventricle, the method comprising the steps of:
  (a) preparing a convex mold having the same shape as the desired artificial ventricle;
  (b) vacuum forming a layer of thermoplastic polymer over said mold;
  (c) removing the mold;
  (d) supporting the layer of thermoplastic vacuum-formed in step (b) on a concave pedestal;
  (e) vacuum forming a thin layer of thermoplastic polymer over the layer of thermoplastic supported by the concave pedestal after said mold has been removed; and
  (f) bonding the periphery of the thin thermoplastic layer formed in step (e) to the outside edge of the layer of the thermoplastic supported by the concave pedestal.

18. A method of manufacturing an artificial ventricle which comprises a housing and a pumping membrane that divides the interior of said housing into a ventricular blood chamber and a drive fluid pumping chamber, the method comprising the steps of:
  (a) preparing a convex mold having the same shape as the desired artificial ventricle;
  (b) vacuum forming a thin layer of thermoplastic polymer over the top portion of said mold so as to form said pumping membrane;
  (c) treating a portion of the convex surface of said pumping membrane with a separating spray;
  (d) vacuum forming a second, thicker layer of thermoplastic polymer over the top portion of said mold and the pumping membrane formed in step (b);
  (e) preparing a concave mold cast from the bottom portion of said convex mold;
  (f) vacuum forming a third, thicker layer of thermoplastic polymer over said concave mold;
  (g) removing both said molds;
  (h) bonding the periphery of said third layer formed in step (f) to the inside periphery of said pumping membrane; and
  (i) sealing said second and third layers together so as to form a fluid tight housing enclosing the pumping membrane therein.

19. A method of manufacturing a ventricular assist device, the method comprising the steps of:
  (a) vacuum forming a housing having an inlet means through which blood is communicated to said housing, an outlet means through which blood is expelled from said housing, and means through which a drive fluid is pumped into and out of said housing;
  (b) vacuum forming a compliance membrane that includes an integral one-way flap valve for controlling the flow of blood through said housing;
  (c) vacuum forming a pumping membrane;
  (d) sealing the compliance membrane within a first portion of said housing so as to form an atrial blood chamber and an atrial compliance chamber that are separated by a fluid tight seal at the periphery of said compliance membrane; and
  (e) sealing the pumping membrane within a second portion of said housing so as to form a ventricular blood chamber and a drive fluid pumping chamber that are separated by a fluid tight seal at the periphery of said pumping membrane.

20. A method as defined in claim 19, wherein step (a) comprises the steps of:
  (a1) preparing a convex mold having the same shape as the desired ventricular assist device;
  (a2) vacuum forming a first layer of thermoplastic polymer over said mold;
  (a3) turning the mold over; and
  (a4) vacuum forming a second layer of thermoplastic polymer over said mold.

21. A method as defined in claim 19, wherein step (a) comprises the steps of:
  (a1) preparing a convex mold having the same shape as the desired ventricular assist device;
  (a2) preparing a concave mold cast from the bottom portion of said convex mold; and
  (a3) vacuum forming a layer of thermoplastic polymer over the top portion of said convex mold and over the concave mold.

22. A method as defined in claim 19, wherein step (b) comprises the steps of:
  (b1) preparing a mold having the same shape as the desired compliance membrane; and
  (b2) vacuum forming a thin layer of thermoplastic polymer over said mold.

23. A method as defined in claim 22, wherein step (b) further comprises the steps of:
  (b3) treating the convex surface of the layer vacuum formed in step (b2) with a lubricant;
  (b4) repeating steps (b2) and (b3) several times to form a multi-layer compliance membrane; and
  (b5) bonding the several layers together at the edges thereof.

24. A method as defined in claim 19, wherein step (c) comprises the steps of:
  (c1) preparing a convex mold having the same shape as the desired pumping membrane; and
  (c2) vacuum forming a thin layer of thermoplastic polymer over said mold.

25. A method as defined in claim 24, wherein step (c) further comprises the steps of:
  (c3) treating the convex surface of the layer vacuum formed in step (c2) with a lubricant;
  (c4) repeating steps (c2) and (c3) several times to form a multi-layer pumping membrane; and
  (c5) bonding the several layers together at the edges thereof.

26. A method as defined in claim 21, wherein step (c) comprises the step of:
  (c1) treating the edges of said layer of thermoplastic polymer vacuum formed in said step (a3) onto said concave mold with an adhesive bonding agent; and
  (c2) vacuum forming a thin layer of thermoplastic polymer onto said layer of thermoplastic polymer previously vacuum formed in said step (a3).

* * * * *

UNITED STATES PATENT AND TRADEMARK OFFICE
CERTIFICATE OF CORRECTION

PATENT NO. : 4,427,470
DATED : January 24, 1984
INVENTOR(S) : Willem J. Kolff

It is certified that error appears in the above-identified patent and that said Letters Patent is hereby corrected as shown below:

Column 7, line 54, "ventrical" should be "ventricle."

Column 11, line 51, "sheel" should be "shell."

Signed and Sealed this

Second Day of October 1984

[SEAL]

Attest:

Attesting Officer

GERALD J. MOSSINGHOFF

Commissioner of Patents and Trademarks